United States Patent
Schmid et al.

(10) Patent No.: US 7,056,437 B2
(45) Date of Patent: Jun. 6, 2006

(54) METHOD AND DEVICE FOR THE TREATMENT OF EFFLUENT, SLUDGE AND ORGANIC SUBSTRATES

(75) Inventors: Andreas Schmid, Münchberg (DE); Wolfgang Geier, Hof (DE)

(73) Assignee: EMU Unterwasserpumpen GmbH, Hof (DE)

( * ) Notice: Subject to any disclaimer, the term of this patent is extended or adjusted under 35 U.S.C. 154(b) by 93 days.

(21) Appl. No.: 10/491,673

(22) PCT Filed: Nov. 8, 2002

(86) PCT No.: PCT/DE02/04127

§ 371 (c)(1),
(2), (4) Date: Apr. 1, 2004

(87) PCT Pub. No.: WO03/042109

PCT Pub. Date: May 22, 2003

(65) Prior Publication Data

US 2004/0256314 A1 Dec. 23, 2004

(30) Foreign Application Priority Data

Nov. 12, 2001 (DE) ................. 101 55 161

(51) Int. Cl.
*C02F 1/34* (2006.01)
*C02F 11/00* (2006.01)

(52) U.S. Cl. ..................... 210/603; 210/252

(58) Field of Classification Search ............... 210/603, 210/608, 173, 252, 767

See application file for complete search history.

(56) References Cited

U.S. PATENT DOCUMENTS

| | | | |
|---|---|---|---|
| 4,341,632 A | 7/1982 | Gregor et al. | |
| 4,906,387 A | 3/1990 | Pisani | |
| 4,990,260 A | 2/1991 | Pisani | |
| 5,326,468 A | 7/1994 | Cox | |
| 5,494,585 A | 2/1996 | Cox | |
| 6,200,486 B1 | 3/2001 | Chahine et al. | |
| 6,395,175 B1* | 5/2002 | Gao et al. | 210/610 |
| 6,491,829 B1* | 12/2002 | Suzuki et al. | 210/749 |
| 6,905,609 B1* | 6/2005 | Nassef | 210/760 |
| 2002/0096456 A1 | 7/2002 | Kim et al. | |

FOREIGN PATENT DOCUMENTS

DE 26 52 229 5/1978

(Continued)

OTHER PUBLICATIONS

Muller, et al., *Wasser Abwasser Praxis*, pp. 25-31 (Mar. 1999).

(Continued)

*Primary Examiner*—Fred G. Prince
(74) *Attorney, Agent, or Firm*—Elliot M. Olstein; Raymond J. Lillie

(57) ABSTRACT

The invention concerns a method of treating filamentous and flocculating microorganism-bearing effluent, sludge or organic substrates used in biogas installations, for reducing or avoiding the formation of bulking sludge, floating sludge and/or foam, wherein the effluent, sludge or organic substrates is or are guided in a flow passage and in the flow passage subjected to a shear loading which is sufficient to reduce the relative ratio of the number of filamentous microorganisms in relation to flocculating microorganisms. The invention further concerns an apparatus for carrying out the method.

22 Claims, 6 Drawing Sheets

FOREIGN PATENT DOCUMENTS

Figure 1:
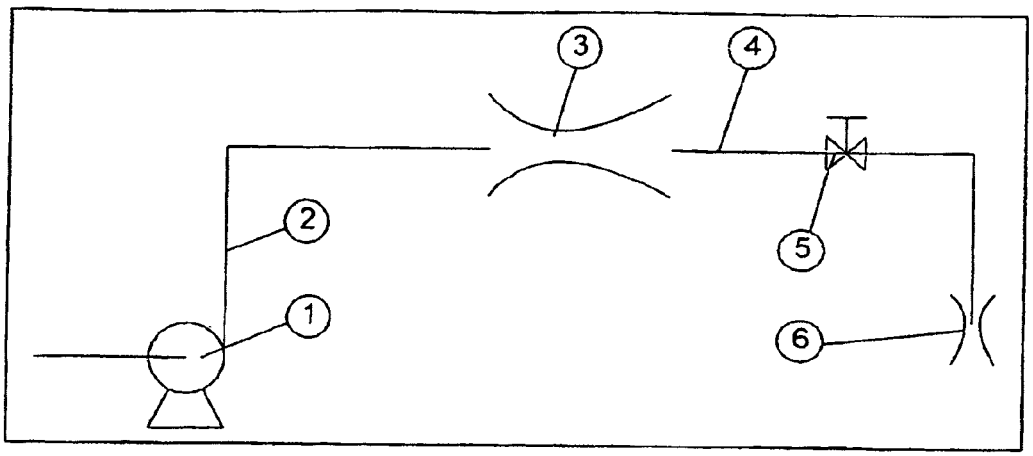

| | | | |
|---|---|---|---|
| DE | 3903648 | A1 | 8/1990 |
| DE | 4114694 | | 11/1992 |
| DE | 4400149 | A1 | 7/1995 |
| DE | 4434540 | A1 | 3/1996 |
| DE | 19502856 | A1 | 8/1996 |
| DE | 19517381 | | 11/1996 |
| DE | 19843862 | | 3/2000 |
| DE | 19936207 | A1 | 2/2001 |
| DE | 10019918 | A1 | 10/2001 |
| DE | 10030241 | A1 | 1/2002 |
| GB | 1589551 | | 5/1981 |
| JP | 5.337491 | | 12/1993 |
| RU | 2090253 | C1 | 9/1997 |
| SU | 719702 | | 3/1980 |
| SU | 1404467 | A1 | 6/1988 |
| WO | WO00/07941 | | 2/2000 |

OTHER PUBLICATIONS

Muller, et al., *Wasserwiirtschaft Abwasser, Abfall*, vol. 47, No. 4, pp. 570-576 (2000).

Schmelz, et al., "Klarschlammvermlnderung durch vershiedene Methoden der Desintegration auf der Klaranlage Schermbeck," pp. 205-224 (Sep. 21, 2000).

*Wasserwirtschaft, Abwasser, Abfall*, vol. 48, No. d, pp. 598-604 (2001).

Abstract from Polytechnichesky Slovar, red. I.I. Artobolevsky, Moskva, Sovetskaya Entisklopedia, 1977, c.193-194, Fig.

Polytechnichesky Solvar, red. I.I.Artobolevsky, Moskva, Sovetskaya Entsiklopedia, 1977, c.248, Fig.

\* cited by examiner

METHOD AND DEVICE FOR THE TREATMENT OF EFFLUENT, SLUDGE AND ORGANIC SUBSTRATES

The invention concerns a method of treating filamentous and flocculating microorganism-bearing effluent, sludge or organic substrates used in biogas installations, for reducing or avoiding the formation of bulking sludge, floating sludge and/or foam.

Sewage installations with biological purification stages repeatedly involve operational problems which are to be attributed to non-sedimenting or floating sludge aggregates, in particular in the activated sludge tank and in the post-settlement or final sedimentation tank.

For stable operation of a sewage installation, it is necessary for the biomass which is used for purification of the effluent and which includes the microorganisms used for the purification operation to be separated from the purified effluent. In the activated sludge process the biomass is generally separated by sedimentation in a post-settlement tank and partially or completely returned to the activated sludge tank. Trouble-free operation of a sewage installation with a biological purification stage therefore requires a biomass which sediments well or an activated sludge which sediments well.

The biomass used in the activated sludge tank is a mixed biocoenosis of the most widely varying microorganisms. The mixed biocoenosis contains inter alia filamentous bacteria or filament bacteria and flocculating bacteria.

Non-sedimenting or floating sludge aggregates occur in the event of increased growth of filamentous bacteria which then aggregate to form a filament mesh. That filament mesh considerably impedes the thickening and settlement process of the activated sludge. The floating sludge aggregates predominantly consist of bulking sludge, floating sludge and foam.

Bulking sludge, floating sludge and foam can further occur if the effluent contains finely distributed small gas bubbles, hydrophobic effluent components and/or cell structures as well as surface-active substances.

Stable operation of a biological sewage installation is made very difficult or is impossible in the event of formation of bulking sludge, floating sludge or foam.

DE 198 43 862 A1 discloses a method of preventing the formation of floating and/or bulking sludge in sewage installations, in which the biomass-bearing sludge is treated with ultrasound.

DE 195 17 381 C1 discloses a further apparatus for destroying cellular structures in sludges of biological sewage installations, using ultrasonic treatment.

A disadvantage is that those processes are complicated and expensive from a technical point of view and increased levels of demand are made on the operating personnel.

KA-Wasserwirtschaft, Abwasser, Abfall 2001 (48) No 5, pages 598 through 604, discusses the use of filling and flocculating agents on a poly-aluminum base, such as for example poly-aluminum hydroxide or poly-aluminum chlorides. The use of such filling and flocculating agents however entails a considerable increase in costs.

WAP (Wasser Abwasser Praxis) 3/99, pages 25 through 31, discloses that mechanically reducing the size of bulking and floating sludges produces smaller aggregates which have improved sedimentation properties.

The operation of reducing the size of bulking and floating sludge is effected using an agitator ball mill, a shearing gap homogeniser, an ultrasonic homogeniser and a high pressure homogeniser. In order to be able to conduct effective treatment of the floating sludge, an energy input of at least about 1000 kJ/m$^3$ of sludge is required.

A disadvantage here is that the crushing apparatuses proposed in that publication are complicated and cost-intensive and are therefore not suitable in particular for many small municipal sewage installations.

The object of the invention is to provide a method and an apparatus which are simple to handle and inexpensive to operate and which effectively reduce or prevent the formation of non-sedimenting sludge aggregates in sewage installations, biogas reactors and so forth.

The object of the invention is attained by a method of treating filamentous and flocculating microorganism-bearing effluent, sludge or organic substrates used in biogas installations, for reducing or avoiding the formation of bulking sludge, floating sludge and/or foam, wherein the effluent, sludge or organic substrates is or are guided in a flow passage and in the flow passage subjected to a shear loading which is sufficient to reduce the relative ratio of the number of filamentous microorganisms in relation to flocculating microorganisms.

Preferred developments are recited in appendant claims 2 through 14.

The invention is described hereinafter substantially with reference to sewage installations. The invention however is in no way limited to sewage installations. Rather the invention can be used in other biological installations in which filamentous and flocculating microorganisms are present and co-operate in a mixed biocoenosis. The invention for example can also be used in relation to biogas reactors and anaerobic fermenters. In that respect the information set out hereinafter correspondingly applies to biogas reactors and anaerobic fermenters.

The effluent in accordance with the invention is preferably an activated sludge or a mixed biocoenosis in biological sewage installations.

In accordance with the present invention the problem, which has existed for decades, of the occurrence of bulking sludge, floating sludge and foam in biological purification stages of sewage installations can be resolved in a surprisingly simple manner.

In accordance with the present invention the effluent, preferably activated sludge or a mixed biocoenosis, is subjected in a flow passage to a shear loading by hydrodynamically produced shearing fields. The shearing fields occur due to speed gradients which occur in the effluent, preferably activated sludge or a mixed biocoenosis, which is guided in the flow passage.

The shear loading results in a reduction in size or division of filament meshes or sludge aggregates formed from long-filamentous microorganisms. In addition finely distributed gas bubbles which adhere to or are enclosed in those sludge aggregates are liberated. Those gas bubbles contained in the untreated sludge aggregates contribute to adversely affecting the sedimentation behaviour of the sludge aggregates.

Finally, due to the shear loading, the procedure involves partial destruction of the filamentous bacteria and a reduction in the filament length of the filamentous bacteria.

The stress applied by the produced shearing field to the filamentous bacteria contained in the mixed biocoenosis results in particular in changes in the metabolism of the filamentous bacteria, which results in a variation in the growth kinetics in relation to the filamentous microorganisms or bacteria. The growth of the filamentous microorganisms is markedly reduced.

The change in the metabolism of filamentous microorganisms is to be attributed in particular to the stimulation of protective mechanisms with respect to the stress produced by the applied shear loading. That results inter alia in a secretion of extracellular polymer substances which are also referred to as EPS, predominantly due to the filamentous microorganisms. The secreted extracellular polymer substances advantageously provide for adhesion of the sludge aggregates which are reduced in size in the shearing field. That adhesion counteracts the occurrence of small sludge particles which do not sediment or which sediment excessively slowly, and it results in advantageous flocculation and accordingly the desired sedimentation of the mixed biocoenesis.

The relative proportions of flocculating microorganisms to filamentous microorganisms in the mixed biocoenosis or activated sludge alter to the advantage of the flocculating microorganisms. An increase in the ratio of flocculating bacteria to filamentous bacteria in the mixed biocoenosis promotes sedimentation of the sludge aggregates.

Flocculating microorganisms exhibit a good sedimentation behaviour, unlike filamentous microorganisms.

Preferably the shear loading is produced by a turbulent flow in the flow passage. It is further preferred that at least one constriction through which the effluent is guided is arranged in the flow passage.

The effluent which is guided in the flow passage is highly turbulent. The Reynolds number of the turbulent effluent or the mixed biocoenosis is preferably at least 100,000, further preferably at least 180,000, still further preferably at least 250,000, still more preferably at least 500,000.

The effluent, preferably activated sludge or a mixed biocoenosis, can be pumped through the flow passage by means of a conventional pump. In that case the at least one constriction can be arranged both at the pressure side and also at the suction side in the flow passage.

In a preferred embodiment the flow speed of the effluent is increased when passing through the constriction in the flow passage under a decreasing pressure until vapor pressure is reached, which occurs in the form of cavitation.

The occurrence of cavities in liquids and the movement thereof is referred to as cavitation. The cavity can be ruptured by a local reduced-pressure phase, shear stresses or an energy input into the liquid. The gases dissolved in the liquid diffuse into the bubbles produced in that way. When the pressure in the liquid rises again, the gas bubbles collapse due to the external pressure. During bubble collapse the bubble content is compressed so greatly that high pressures, up to some 1000 bars, and high temperatures, up to several 1000 K, are locally produced. The gas is ionised in the bubble and radicals are produced.

In addition during the collapse the bubble emits shock waves and, if it is in the proximity of solid surfaces, a liquid jet which passes through the bubble. The liquid jets and shock waves emitted by the bubbles have the power to break up particle agglomerates such as for example sludge agglomerates and to break open macromolecules and bacterial cell walls.

In the constriction arranged in the flow passage, the flow speed increases and the pressure falls. It is under those conditions that cavitation which is desired in relation to the method according to the invention occurs.

In an embodiment, the method according to the invention preferably involves joint occurrence of a shear loading and cavitation.

The shear loading produced for example by a highly turbulent flow as well as the cavitation preferably produced by the constriction in the flow passage extremely advantageously co-operate in the method according to the invention.

The shear loading and the cavity effect act in particular on the relatively large filamentous microorganisms or on the filament meshes formed by the filamentous microorganisms. The filamentous microorganisms are partially destroyed by the cell membranes being broken open. For a substantial part the procedure involves a reduction in the length of the filaments, and thus entails the filament mesh being broken open or reduced in size.

Surprisingly the flocculating bacteria are not destroyed by the method according to the invention. In addition, no substantial change in cell metabolism occurs, so that the growth kinetics of the flocculating microorganisms are not substantially impaired or not substantially altered. Thus, in regard to the different growth kinetics of filamentous and flocculating microorganisms, the method according to the invention results in an advantageous change in the composition of the mixed biocoenosis. That change in bacterial composition, which is caused by the method according to the invention, therefore results in making the activated sludge sound.

In accordance with a further embodiment of the invention the duration of cavitation and thus the period of action of cavitation on the effluent or the mixed biocoenosis is adjustable.

It was surprisingly discovered that the cavitation produced by the constriction in the flow passage can be achieved if the inside diameter of the flow passage which is preferably arranged downstream of the constriction in relation to the direction of flow of the effluent is greater than the smallest inside diameter of the constriction in the flow passage but smaller than the inside diameter of the flow passage which is disposed upstream of the constriction.

The duration of cavitation can be controlled by way of the length of the flow passage arranged downstream of the constriction. If the flow passage arranged downstream of the constriction is increased in length, the period of action on the effluent, preferably the activated sludge or the mixed biocoenosis, is also increased.

The ratio of the inside diameter of the flow passage upstream of the constriction, with respect to the direction of flow of the effluent, to the inside diameter of the flow passage downstream of the constriction can be for example between about 5:1 and about 1.2:1, preferably between 3:1 and 1.5:1, very preferably 2:1.

The ratio of the smallest inside diameter of the constriction to the inside diameter of the flow passage arranged at the downstream side in relation to the constriction can be for example between 1:1.2 and 1:3, preferably 1:2.

It is extremely surprising that abrasion is not caused by the cavitation produced, in the method according to the invention, either at the constriction in the flow passage or at the flow passage arranged downstream thereof in the direction of flow of the effluent, with fittings which are possibly arranged there.

It is assumed that the cavitation bubbles, by virtue of the higher pressure at the wall of the flow passage, occur predominantly in the middle of the flow passage. The cavitation bubbles occurring in the middle of the effluent flow accordingly do not come into contact with the wall of the flow passage and in that respect cannot give rise to an abrasion effect.

In the simplest case the flow passage can be in the form of a conduit. The constriction in the flow passage in the simplest case can be in the form of a nozzle, preferably with the geometry of a Laval nozzle.

The object of the invention is further attained by an apparatus for the treatment of filamentous and flocculating microorganism-bearing effluent, sludge or organic substrates used in biogas installations, for reducing or avoiding the formation of bulking sludge, floating sludge and/or foam, wherein the apparatus has a flow passage having at least one constriction, and a device for conveying effluent, sludge or organic substrates through the flow passage.

Preferred developments of the apparatuses are recited in appendant claims 11 through 22.

In regard to the ratio of sizes of the inside diameters of the flow passage at the constriction of the flow passage or upstream and downstream of the constriction, attention is directed to the foregoing information relating to the method according to the invention.

It is preferred if the at least one constriction includes a portion having a converging and a diverging inside diameter, wherein, with respect to the direction of flow of the effluent, preferably activated sludge or a mixed biocoenosis, the portion of a converging inside diameter is arranged upstream of the portion of a diverging inside diameter.

The flow passage for example, with respect to the direction of flow of the effluent, can firstly conically constrict to a smallest inside diameter and subsequently conically enlarge. The constriction is preferably a nozzle which intercommunicates two flow passages, preferably conduits.

In a further embodiment of the invention the constriction or the nozzle is so designed that the length of the portion of converging inside diameter is shorter than the length of the portion of diverging inside diameter.

In this embodiment the geometrical configuration of the constriction or the nozzle is accordingly not symmetrical with respect to the portion of the smallest inside diameter of the constriction or the nozzle.

It has been found that, when the nozzle is of an asymmetrical configuration, the desired cavitation can be so set that cavitation which is suitable for the purposes of preventing bulking sludge, floating sludge and/or foam is produced. In particular the length of subsequent cavitation formation and accordingly the period of action of cavitation on the effluent, can be controlled by way of the exit angle of the nozzle.

In accordance with a preferred embodiment the nozzle involves the geometry of a Laval nozzle.

In a further embodiment of the apparatus according to the invention arranged downstream of the constriction or the nozzle in the flow passage is a throttle, for example a slider. The occurrence of cavitation can be additionally controlled by way of that throttle.

Gas bubbles which pass into the flow passage can exert a damping effect on cavitation formation. In that respect, in accordance with a preferred embodiment, the proportion of gas bubbles in the effluent which is introduced into the flow passage is reduced. Preferably, the effluent is degassed while it is being conveyed into the flow passage, for example by the use of a pump, preferably an immersed motor pump, in an immersed shaft.

Figure 2:
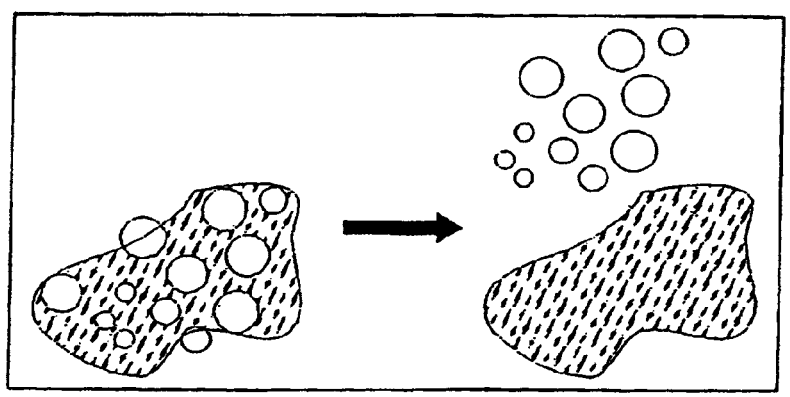
Figure 3:
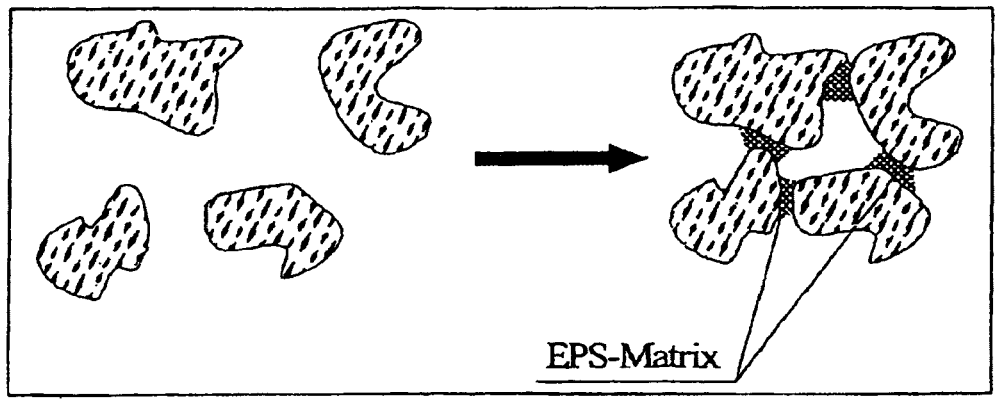
Figure 4:
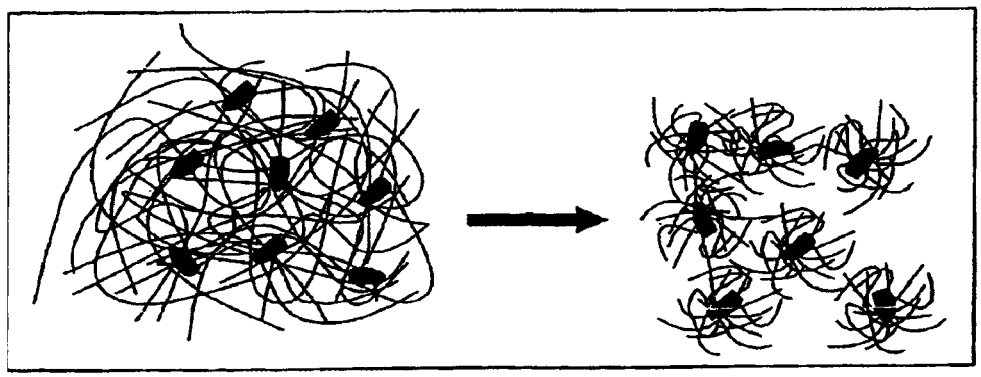
Figure 5:
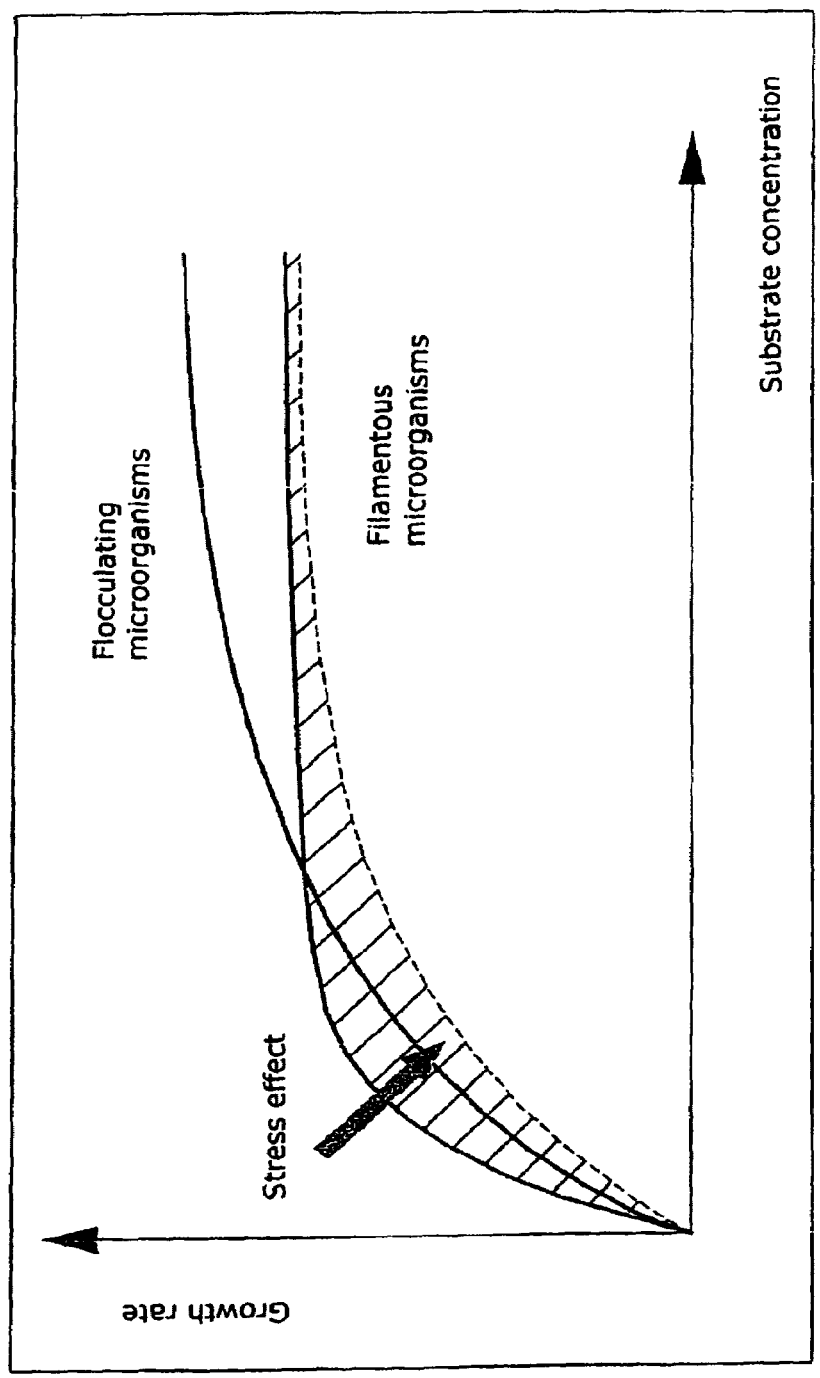
Figure 6:
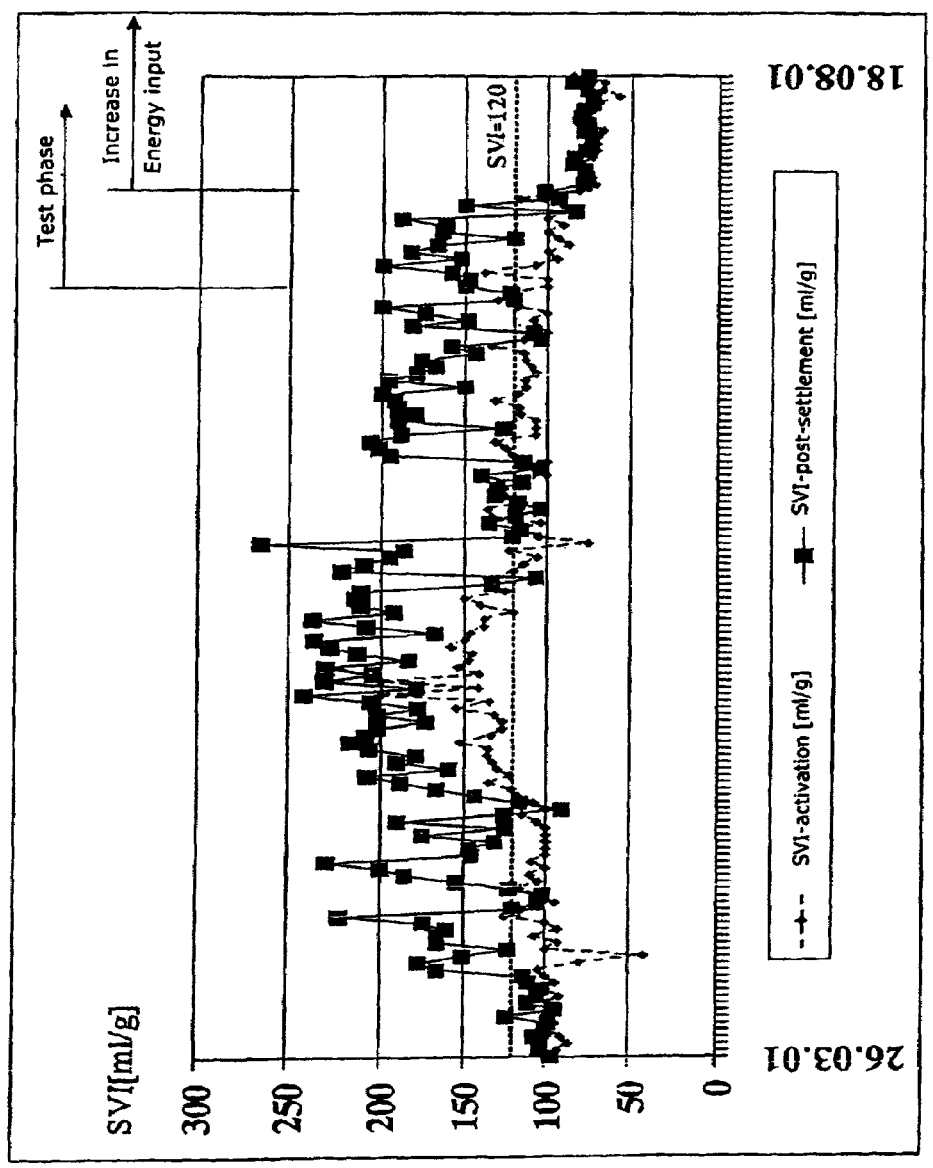
Figure 7:
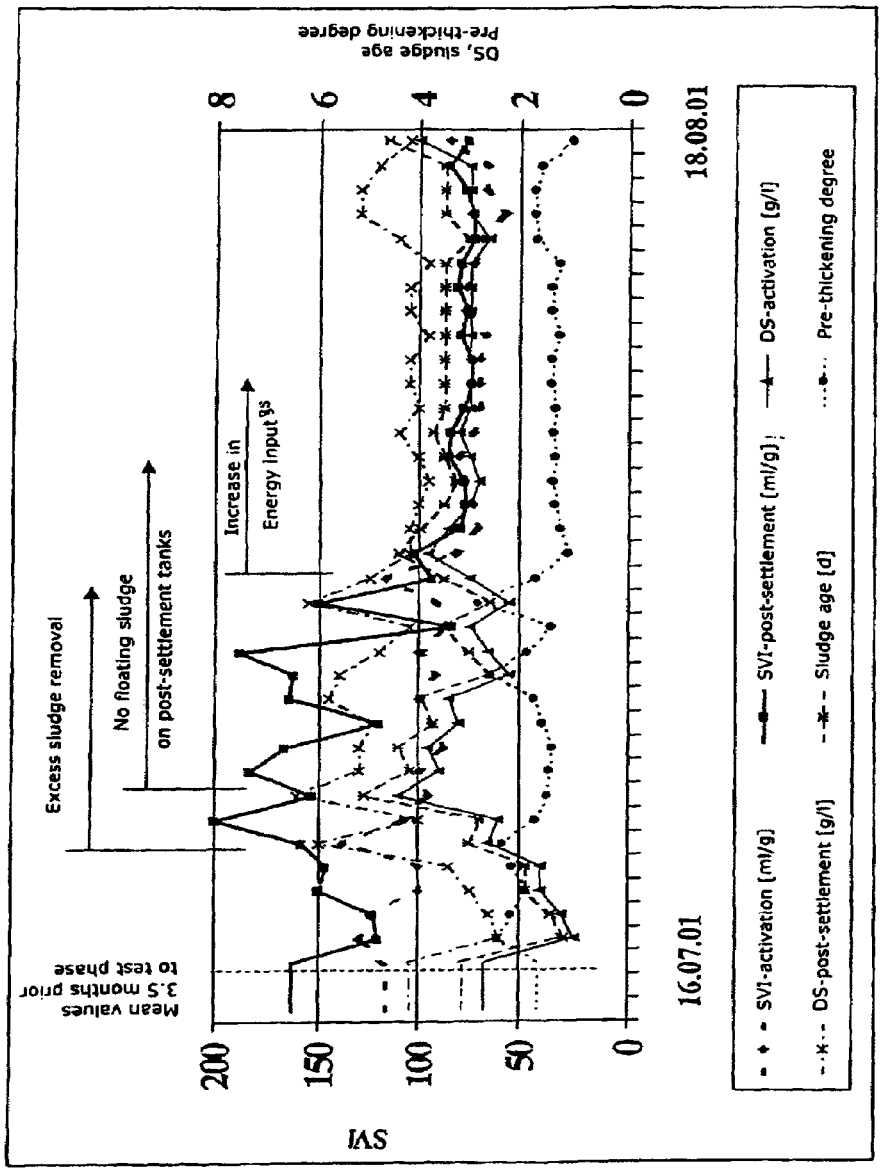
Figure 8:
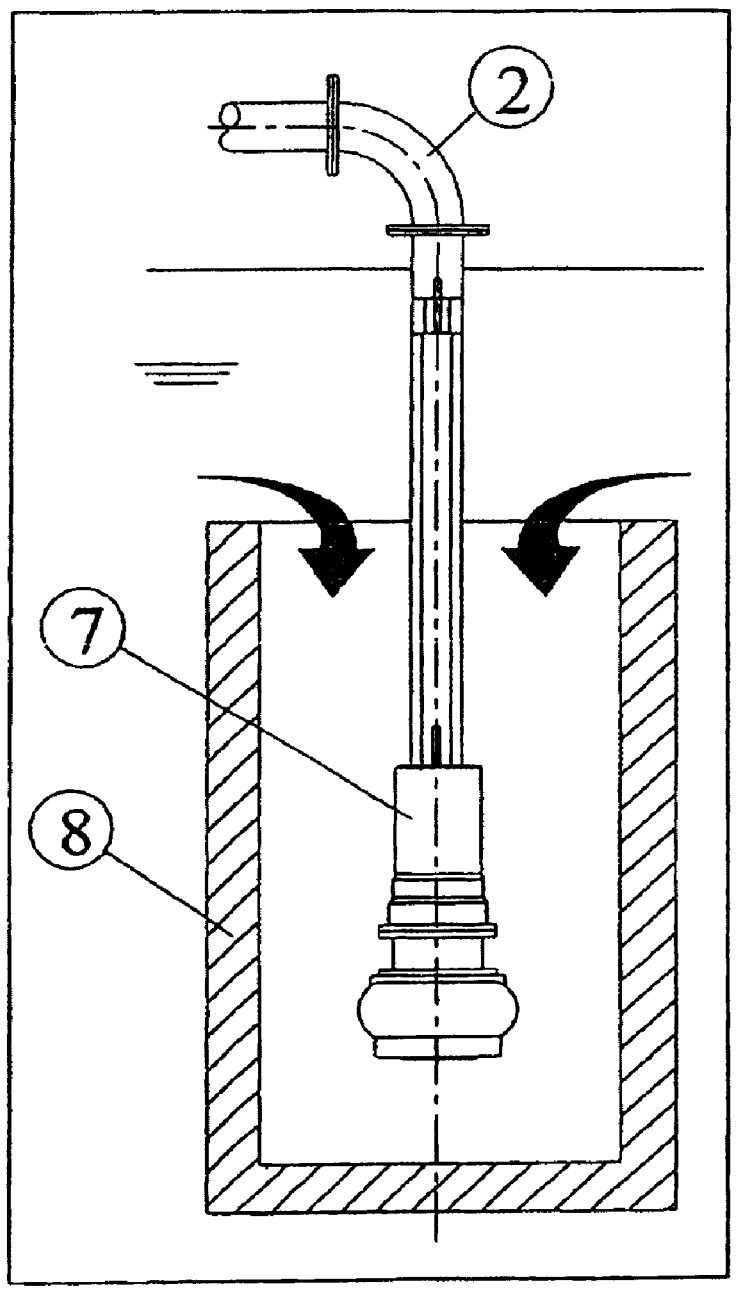

The invention is further illustrated hereinafter with reference to FIGS. 1 through 8 in which:

FIG. 1 is a diagrammatic view of a structure by way of example of an apparatus according to the invention, FIG. 2 is a diagrammatic view of degassing of sludge aggregates in the shearing field, FIG. 3 is a diagrammatic view of improved flocculation of reduced-size sludge aggregates, which is produced by the secretion of extracellular polymer substances (EPS), FIG. 4 is a diagrammatic view of a reduction in the length of the filaments of filamentous microorganisms in the shearing field and possibly by cavitation, FIG. 5 is a diagrammatic view of the influence of the method according to the invention on the growth kinetics of flocculating microorganisms and filamentous microorganisms, FIG. 6 is a view showing measurement values of the sludge volume index (SVI) prior to and after use of the method according to the invention in a test sewage installation, FIG. 7 is a view of measurement values which show stabilisation of the process parameters by the method according to the invention, in a test sewage installation, and FIG. 8 is a diagrammatic view of a pump arranged in an immersed shaft.

FIG. 1 shows a diagrammatic view of the apparatus according to the invention. The pump 1 conveys effluent, preferably activated sludge or a mixed biocoenosis, for example out of an activation tank or a post-settlement tank (not shown) by way of a conduit 2 through a nozzle 3 into a conduit 4. A throttle 5 can be provided in the conduit 4. The treated effluent subsequently passes out of the conduit 4 by way of a discharge device 6, preferably back into the removal tank, that is to say for example the activation tank or the post-settlement tank. It will be appreciated that the treated effluent can also be discharged by way of the discharge device 6 into a further catch tank.

The pump 1 can be arranged both upstream of the nozzle 3 and also downstream of the nozzle 3 in the conduit 2 or 4. The conduit 2 is of an inside diameter which is preferably larger than the inside diameter of the conduit 4, the inside diameter of the conduit 4 being larger than the smallest inside diameter of the nozzle 3.

Any pump suitable for use in a settlement tank can be used as the pump 1. The conduit 4 which is arranged on the downstream side of the nozzle 3, by virtue of the inside diameter which is reduced in relation to the conduit 2 arranged on the upstream side in relation to the nozzle 3, has a prolonged period of action of the cavitation produced in the nozzle 3, on the effluent or the mixed biocoenosis. The length of the conduit 4 can be adjusted in dependence on the desired period of action of cavitation. For example the length of the conduit 4 can be variably adjustable. That makes it possible to achieve a desired reduction in the filament length of filamentous bacteria and also reliable liberation of the gas bubbles enclosed in the filament mesh produced by the filamentous microorganisms. In addition, growth of the filamentous microorganisms is slowed down by the stress applied thereto.

The period of action of cavitation can be controlled inter alia by way of the length of the conduit 4 arranged at the downstream side of the nozzle 3. In addition, the formation of cavitation bubbles can also be controlled by the pressure in the conduit 4, which pressure is adjustable by the throttle flap 5. The discharge device 6 which is preferably in the form of a spray nozzle, upon discharge of the treated mixed biocoenosis from the apparatus according to the invention, causes the gas bubbles dissolved from the sludge aggregates to escape.

It is possible to arrange upstream of the nozzle 3 a confuser which reduces the inside diameter of the conduit 2 supplying the effluent, that is to say the conduit 2 arranged at the upstream side in relation to the nozzle. That improves the transition between the effluent-supplying conduit 2 and the nozzle 3.

It is further preferred if a diffuser is arranged between the nozzle 3 and the throttle flap 5, the diffuser enlarging the inside diameter of the conduit 4 arranged at the downstream side of the nozzle 3. The enlargement of the inside diameter of the conduit 4 causes the pressure in the effluent, preferably activated sludge or a mixed biocoenosis, to be increased, and cavitation terminated. In that way, it is possible to reliably prevent the action of cavitation, that is to say the occurrence of cavitation bubbles, on the throttle flap 5, and accordingly damage, for example abrasion, at the throttle flap 5.

Preferably the inside diameter of the conduit 4 downstream of the diffuser is enlarged to an inside diameter which approximately corresponds to the inside diameter of the conduit 2 arranged at the upstream side in relation to the nozzle 3.

The duration of the cavitation effect and thus the period of action of cavitation can be controlled by way of the length of the conduit 4 of a reduced inside diameter between the nozzle 3 and the diffuser. The length of the conduit 4 between the nozzle 3 and the diffuser can be adapted to be variable, for example it can be telescopic.

In principle it is also possible for a plurality of nozzles 3, for example two or three nozzles, to be arranged in succession in a conduit system. It has been found however that a reduction in the occurrence of bulking sludge, floating sludge and/or foam, or prevention of the occurrence of bulking sludge, floating sludge and/or foam, is already achieved with one nozzle 3, by the configuration according to the invention.

The apparatus according to the invention is surprisingly simple from the structural point of view. Accordingly the method and the apparatus according to the invention are extremely advantageous in regard to a substantially maintenance-free and accordingly inexpensive operation. Advantageously, there is no need for trained personnel for operation. In that respect the present invention can advantageously be used both in relation to large and also in relation to small sewage installations.

FIG. 2 shows a diagrammatic view illustrating the liberation of gas bubbles which adhere to or are enclosed in sludge aggregates and which are liberated from the sludge aggregates by the action of a shearing field thereon. The buoyancy of the sludge aggregates is substantially reduced by virtue of liberation of the gas bubbles which adhere to or are enclosed in the sludge aggregates.

When the effluent, preferably the activated sludge or the mixed biocoenosis, flows through the nozzle 3, that further involves a reduction in pressure in the effluent flowing therethrough, which further promotes detachment of the gas bubbles from the sludge aggregates. In other words, co-operation of the turbulence induced by the nozzle 3 in the effluent, with the reduction in pressure, results in a desired degassing effect in respect of the sludge aggregates or liberation of the adhering or enclosed gas bubbles.

FIG. 3 shows the improved flocculation of reduced-size sludge aggregates, which is produced by the secretion of extracellular polymer substances (EPS) by filamentous microorganisms. The microorganisms contained in the effluent are subjected to a stress due to the shear loading, induced in the nozzle 3, in respect of the effluent, preferably the activated sludge or the mixed biocoenosis. In the case of microorganisms that stress induces the secretion of EPS. The secretion of EPS results in floc-like adhesion of reduced-size sludge aggregates.

That flocculation effect is highly advantageous in regard to the desired sedimentation of the sludge. The assembly of reduced-size sludge aggregates, which is caused by EPS, opposes the formation of excessively small flocs which, by virtue of the excessively small size, do not sediment or do not sediment within a desired period of time.

FIG. 4 diagrammatically shows the reduction in the length of the filaments of filamentous microorganisms by application of the method according to the invention. Besides the reduction in filament length, the filament mesh formed is also broken open.

FIG. 5 shows the influence of the method according to the invention on the growth kinetics of flocculating microorganisms and filamentous or thread-shaped microorganisms. FIG. 5 shows that the growth rate of flocculating microorganisms is not or is not substantially influenced by the method according to the invention.

In contrast the method according to the invention has a marked influence on the growth rate of filamentous microorganisms. Due to the shearing field applied in the apparatus according to the invention and the cavitation effect which preferably occurs, the growth of filamentous microorganisms is markedly restrained in comparison with flocculating microorganisms. That results in a desired change in the relative composition of the mixed biocoenosis. The relative ratio of filamentous microorganisms to flocculating microorganisms is reduced.

FIGS. 6 and 7 show measurement curves which were measured in a test sewage installation.

The method according to the invention was carried out in a sewage installation with about 12,000 connected inhabitant equivalents. The effluent in the feed to that installation was severely loaded with effluents from the textile industry and for more than 10 years had resulted in major bulking sludge and floating sludge problems.

In the test sewage installation the sludge volume index (SVI) was frequently above a value of 120 ml/g. The sludge cover which is formed on the post-settlement tank was removed up to three times daily. The thickness of the floating sludge cover could increase to 5 cm and more.

The apparatus according to the invention was arranged directly in the activation tank of the sewage installation. Within the first two weeks the apparatus according to the invention was operated daily only for 4 hours (output power of the pump 3.75 kW at a volume flow of 10.6 l/s). The inside diameter of the conduit arranged upstream of the nozzle was 100 mm, the inside diameter of the conduit arranged downstream of the nozzle was 50 mm. The narrowest diameter of the nozzle used was 25 mm. The nozzle involved the geometry of a Laval nozzle.

Arranged upstream of the nozzle was a confuser which reduced the inside diameter of the supplying conduit from 100 mm to 50 mm. A throttle was arranged in the conduit at the downstream side of the nozzle. Arranged between the nozzle and the throttle was a diffuser which enlarged the inside diameter of the conduit from 50 mm to 100 mm again. The spacing between the nozzle and the diffuser or the length of the conduit with a 500 mm inside diameter was 100 cm.

After just 3 days of a test period it was possible to microscopically observe a markedly reduced filament length of long-filament structures in the activated sludge. That fact made itself noticeable in a gradually decreasing sludge volume index (SVI).

After 2 weeks of test the apparatus according to the invention was switched over to continuous operation and the energy input was increased to about 350 kJ/m$^3$ mixed biocoenosis (FIG. 6).

The sludge volume index (SVI) which describes the volume of the sedimented sludge of 1 l content after 30 minutes sedimentation, in relation to the initial concentration, has fallen to markedly below 100 ml/g after the increase in energy input. At values above 120 ml/g, considerable problems can occur in regard to the settlement properties of the bulking sludge in the post-settlement tank.

A drastic reduction in length of the filament length of filamentous microorganisms could already be microscopically observed on the following day. The sludge volume index was of a value of about 80 ml/g and maintained that value over the coming weeks. That value is markedly below the threshold value of 120 ml/g, as from which bulking sludge behaviour is to be expected. A significant reduction in the sludge volume index to about 80 ml/g occurred both in the activation tank and also in the post-settlement tank.

It was completely surprisingly found that the energy input into the mixed biocoenosis can be markedly below 1000 kJ/m$^3$ in order to avoid the occurrence of bulking and floating sludge. In dependence on the proportion of filamentous microorganisms in the mixed biocoenosis, the energy input can be for example in a range of between about 200 kJ/m$^3$ mixed biocoenosis and about 800 kJ/m$^3$ mixed biocoenosis, preferably between about 250 kJ/m$^3$ mixed biocoenosis and 600 kJ/m$^3$, further preferably between about 300 kJ/m$^3$ and about 500 kJ/m$^3$. The speed of the effluent or mixed biocoenosis conveyed through the conduit 4 is in that case in a range of between about 3 m/s and 10 m/s, preferably between about 4 m/s and 8 m/s, further preferably between about 5 m/s and 7 m/s.

It can be seen from FIG. 7 that a stabilisation effect also occurred with further process parameters, that is to say the method according to the invention resulted in stable operation of the test installation.

It can be clearly seen that excess sludge could be drawn off by virtue of the improved settlement properties and thus stabilisation of all process parameters occurred. Upon an increase in the energy input to about 350 kJ/m$^3$ by increasing the pump power, that produced smoothing of the measurement curves obtained, that is to say in relation to the sludge index in the activation tank (SVI-activation), the sludge index in the post-settlement tank (SVI-post-settlement), dry substance in the activation tank (DS-activation), dry substance in the post-settlement tank (DS-post-settlement), in relation to the sludge age and in relation to the degree of pre-thickening. The mixed biocoenosis is markedly improved.

FIG. 8 shows a pump 7 arranged in a shaft 8 disposed under the surface of the mixed biocoenosis. The shaft 8 is identified in accordance with the invention as an immersed shaft 8. Arranged in the immersed shaft 8 is a pump 7 which conveys the effluent, preferably the activated sludge or the mixed biocoenosis, into the conduit 2. Between the pump 7 and the inside walls of the immersed shaft 8, a degassing zone is formed. In the degassing zone, gas bubbles contained or entrained in the effluent or the mixed biocoenosis are at least partially separated off and liberated, and escape through the shaft which is open in the direction towards the surface.

The invention claimed is:

1. A method of reducing or avoiding the formation of bulking sludge, floating sludge and/or foam, wherein filamentatious and flocculating microorganism-bearing effluent, sludge or organic substrates used in biogas installations are treated, characterised in that the effluent, sludge or organic substrates is or are guided in a conduit (2, 4) and through at least one constriction (3) arranged in the conduit (2, 4) and is or are subjected to a shear loading which is sufficient to reduce the relative ratio of the number of filamentous microorganisms in relation to flocculating microorganisms, wherein the shear loading is produced by a turbulent flow in the conduit, and wherein the flow speed of the effluent, the sludge or the organic substrates is increased on passing through the constriction (3) of the conduit (2, 4) under a reducing pressure, wherein subsequently cavitation is produced in the effluent, in the sludge or in the organic substrates.

2. A method as set forth in claim 1 characterised in that the occurrence of cavitation is adjustable insofar as the inside diameter of the conduit (2, 4) is so selected that the inside diameter is at the smallest at the constriction (3) and the inside diameter of the conduit (2) at the upstream side of the constriction (3) of the inside diameter is greater than the inside diameter of the conduit (4) at the downstream side of the constriction (3).

3. A method as set forth in claim 2 characterised in that the duration of cavitation is adjustable by way of the length of the conduit (4) arranged at the downstream side of the constriction (7).

4. A method as set forth in any one of the preceding claims characterised in that the inside diameter of the constriction (3) in the conduit (2, 4) is variable.

5. A method as set forth in claim 1 characterised in that gas bubbles contained or entrained in the effluent, sludge or in the organic substrates are at least partially removed before introduction into the conduit (2, 4).

6. A method as set forth in claim 5 characterised in that the effluent, the sludge or the organic substrates is or are at least partially freed of entrained or contained gas bubbles by being conveyed out of an immersed shaft (8).

7. A method as set forth in claim 1 characterised in that the Reynolds number of the effluent, sludge or organic substrates guided through the conduit (2, 4) is at least 100,000, preferably at least 250,000, further preferably at least 500,000.

8. A method as set forth in claim 1 characterised in that the effluent, the sludge or the organic substrates is or are sprayed after being passed through the conduit (2, 4).

9. A method as set forth in claim 1 through 8 characterised in that the at least one constriction (3) is a nozzle.

10. A method as set forth in claim 1 characterised in that the effluent is activated sludge or a mixed biocoenosis.

11. An apparatus for reducing or avoiding the formation of bulking sludge, floating sludge and/or foam, characterised in that the apparatus has a conduit (2, 4) having at least one constriction (3) and a device (7) for conveying effluent, sludge or organic substrates through the conduit (2, 4) so that the treatment of filamentous and flocculating microorganism-bearing effluent, sludge or organic substrates used in biogas installations is effected under the action of cavitation, and that a throttle (5) is arranged at the downstream side of the constriction (3) in the conduit (4).

12. Apparatus as set forth in claim 11 characterised in that the inside diameter of the conduit (2, 4) is at the smallest at the constriction (3) and the inside diameter of the conduit (2) at the upstream side of the constriction (3) is greater than the inside diameter of the conduit (4) at the downstream side of the constriction (3).

13. Apparatus as set forth in claim 12 characterised in that the ratio of the inside diameter of the conduit (2) upstream of the constriction (3) and the inside diameter of the conduit (4) downstream of the constriction (3) is between about 5:1 and about 1.2:1.

14. Apparatus as set forth in claim 13 characterised in that the ratio is between about 3:1 and about 1.5:1, preferably 2:1.

15. Apparatus as set forth in claim 14 characterised in that the at least one constriction (3) includes a portion with a converging and a diverging inside diameter, wherein the portion of converging inside diameter is arranged at the upstream side and the portion of diverging inside diameter is arranged at the downstream side.

16. Apparatus as set forth in claim 15 characterised in that the length of the portion of converging inside diameter is shorter than the length of the portion of diverging inside diameter.

17. Apparatus as set forth in any one of claims 11 through 16 characterised in that the length of the conduit (4) arranged at the downstream side of the constriction (3) is variably adjustable.

18. Apparatus as set forth in claim 11 characterised in that the constriction (3) is a nozzle.

19. Apparatus as set forth in claim 18 characterised in that a confuser is arranged at the upstream side of the nozzle (3).

20. Apparatus as set forth in claim 11 characterised in that a diffuser is arranged after the conduit (4) at the downstream side of the constriction, preferably upstream of the throttle (5).

21. Apparatus as set forth in claim in 11 characterised in that the device (7) for conveying the effluent, sludge or the organic substrates is a pump.

22. Apparatus as set forth in claim 21 characterised in that the pump is arranged in an immersed shaft (8).

\* \* \* \* \*